United States Patent
Lenker et al.

(10) Patent No.: US 6,355,060 B1
(45) Date of Patent: Mar. 12, 2002

(54) APPARATUS AND METHOD FOR DEPLOYMENT RELEASE OF INTRALUMINAL PROSTHESES

(75) Inventors: Jay A. Lenker, Los Altos Hills; Michael A. Evans, Palo Alto; Steven W. Kim; Brian Glynn, both of Sunnyvale; Gwendolyn A. Watanabe, Mountain View, all of CA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 09/421,202

(22) Filed: Oct. 15, 1999

Related U.S. Application Data

(60) Division of application No. 08/862,085, filed on May 22, 1997, now Pat. No. 6,024,763, which is a division of application No. 08/475,200, filed on Jun. 7, 1995, now Pat. No. 5,683,451, which is a continuation-in-part of application No. 08/388,561, filed on Feb. 13, 1995, now abandoned, which is a continuation-in-part of application No. 08/339,911, filed on Nov. 14, 1994, now abandoned, which is a continuation-in-part of application No. 08/290,021, filed on Aug. 12, 1994, now abandoned, which is a continuation-in-part of application No. 08/255,681, filed on Jun. 8, 1994, now abandoned.

(51) Int. Cl.[7] ................................. A61F 2/00
(52) U.S. Cl. ................... 623/1.34; 604/103.1
(58) Field of Search ............... 623/1.34, 1.11, 623/1.23; 604/103.1

(56) References Cited

U.S. PATENT DOCUMENTS

| | | | |
|---|---|---|---|
| 4,140,126 A | 2/1979 | Choudhury | |
| 4,545,082 A | * 10/1985 | Hood | ............... 623/1.11 |
| 4,562,596 A | 1/1986 | Kornberg | |
| 4,577,631 A | 3/1986 | Kreamer | |
| 4,577,632 A | 3/1986 | Kreamer | |
| 4,617,932 A | 10/1986 | Kornberg | |
| 4,787,899 A | 11/1988 | Lazarus | |
| 4,793,348 A | 12/1988 | Palmaz | |
| 4,820,298 A | 4/1989 | Leveen et al. | |
| 4,886,062 A | 12/1989 | Wiktor | |
| 4,913,141 A | 4/1990 | Hillstead | |
| 4,938,220 A | * 7/1990 | Mueller | ............... 606/194 |
| 4,950,227 A | 8/1990 | Savin et al. | |
| 4,969,890 A | 11/1990 | Sugita et al. | |
| 4,990,151 A | 2/1991 | Wallsten | |
| 5,019,085 A | 5/1991 | Hillstead | |
| 5,035,706 A | 7/1991 | Gianturco et al. | |
| 5,037,427 A | 8/1991 | Harada et al. | |

(List continued on next page.)

FOREIGN PATENT DOCUMENTS

| | | |
|---|---|---|
| EP | 0274846 A1 | 7/1988 |
| EP | 0364420 A1 | 4/1990 |
| EP | 0 461 791 | 12/1991 |

(List continued on next page.)

OTHER PUBLICATIONS

Hawley's Condensed Chemical Dictionary, 12th ed. (1993).

*Primary Examiner*—Michael J. Milano
(74) *Attorney, Agent, or Firm*—Sterne, Kessler, Goldstein & Fox P.L.L.C.

(57) ABSTRACT

A delivery catheter for a radially compressible tubular prosthesis comprises an elongate shaft slidably received within a tubular cover. The prosthesis is carried within a plurality of elongate, relatively hard runners, and is restrained in a radially compressed configuration by the cover. After introducing the catheter to a desired target location within a body lumen, the prosthesis may be released by proximally retracting the cover. The runners may optionally remain disposed about the prosthesis to be retracted separately, or, alternatively, the runners retract proximally with the cover as the prosthesis slides over the hard runner surfaces.

7 Claims, 15 Drawing Sheets

U.S. PATENT DOCUMENTS

| | | |
|---|---|---|
| 5,078,720 A | 1/1992 | Burton et al. |
| 5,078,726 A | 1/1992 | Kreamer |
| 5,089,005 A | 2/1992 | Harada |
| 5,092,877 A | 3/1992 | Pinchuk |
| 5,098,440 A | 3/1992 | Hillstead |
| 5,104,399 A | 4/1992 | Lazarus |
| 5,147,370 A | 9/1992 | McNamara et al. |
| 5,158,548 A | 10/1992 | Lau et al. |
| 5,190,058 A | 3/1993 | Jones et al. |
| 5,192,297 A | 3/1993 | Hull |
| 5,201,757 A | 4/1993 | Heyn et al. |
| 5,211,658 A | 5/1993 | Clouse |
| 5,219,355 A | 6/1993 | Parodi et al. |
| 5,242,399 A | 9/1993 | Lau et al. |
| 5,272,971 A | 12/1993 | Fredericks |
| 5,275,622 A | 1/1994 | Lazarus et al. |
| 5,282,824 A | 2/1994 | Gianturco |
| 5,429,617 A * | 7/1995 | Hammersmark et al. ...... 606/7 |
| 5,433,723 A | 7/1995 | Lindenberg et al. |
| 5,478,349 A | 12/1995 | Nicholas |
| 5,480,423 A | 1/1996 | Ravenscroft et al. |
| 5,489,295 A | 2/1996 | Piplani |
| 5,507,768 A | 4/1996 | Lau et al. |
| 5,562,724 A | 10/1996 | Vorwerk et al. |
| 5,562,726 A | 10/1996 | Chuter |
| 5,609,627 A | 3/1997 | Goicoechea et al. |
| 5,687,723 A * | 11/1997 | Avitall .......................... 606/41 |
| 5,713,913 A * | 2/1998 | Lary ........................... 606/159 |
| 5,851,210 A * | 12/1998 | Torossian ................... 606/108 |

FOREIGN PATENT DOCUMENTS

| | | |
|---|---|---|
| EP | 0466518 A2 | 1/1992 |
| EP | 0466518 A3 | 1/1992 |
| EP | 0505686 A1 | 9/1992 |
| EP | 0508473 A2 | 10/1992 |
| EP | 0518704 A1 | 12/1992 |
| EP | 0518839 A2 | 12/1992 |
| EP | 0533511 A1 | 3/1993 |
| EP | 0536610 A1 | 4/1993 |
| EP | 0539237 A1 | 4/1993 |
| EP | 0 551 179 | 7/1993 |
| EP | 0575719 A1 | 12/1993 |
| EP | 0596145 A1 | 5/1994 |
| EP | 0657147 A2 | 6/1995 |
| RU | 260819 | 1/1970 |
| WO | 9317636 | 9/1993 |
| WO | 9529725 | 11/1995 |
| WO | 9613228 | 5/1996 |
| WO | 9618361 | 6/1996 |

* cited by examiner

APPARATUS AND METHOD FOR DEPLOYMENT RELEASE OF INTRALUMINAL PROSTHESES

CROSS-REFERENCE TO RELATED APPLICATIONS

This is a division of application Ser. No. 08/862,085, filed May 22, 1997, now U.S. Pat. No. 6,024,763 which is a division of application Ser. No. 08/475,200, filed Jun. 7, 1995, now U.S. Pat. No. 5,683,451 which is a continuation-in-part of application Ser. No. 08/388,561, filed Feb. 13, 1995, now abandoned, which is a continuation-in-part of application Ser. No. 08/339,911, filed Nov. 14, 1994, now abandoned, which is a continuation-in-part of application Ser. No. 08/290,021, filed Aug. 12, 1994, now abandoned, which is a continuation-in-part of application Ser. No. 08/255,681, filed Jun. 8, 1994, now abandoned, the disclosures of which are incorporated by reference.

BACKGROUND OF THE INVENTION

1. Field of the Invention

The present invention relates generally to apparatus and methods for the endoluminal placement of resilient tubular prostheses, such as grafts, stents, stent-grafts, and other structures. More particularly, the present invention relates to a delivery catheter for the placing of such intraluminal tubular protheses in body lumens, including blood vessels, for the treatment of abdominal and other aneurysms.

Vascular aneurysms are the result of abnormal dilation of a blood vessel, usually resulting from disease and/or genetic predisposition which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending distally into one or both of the iliac arteries.

Aortic aneurysms are most commonly treated in open surgical procedures where the diseased vessel segment is bypassed and repaired with an artificial vascular graft. While considered to be an effective surgical technique, particularly considering the alternative of a usually fatal ruptured abdominal aortic aneurysm, conventional vascular graft surgery suffers from a number of disadvantages. The surgical procedure is complex and requires experienced surgeons and well equipped surgical facilities. Even with the best surgeons and equipment, however, patients being treated frequently are elderly and weakened from cardiovascular and other diseases, reducing the number of eligible patients. Even for eligible patients prior to rupture, conventional aneurysm repair has a relatively high mortality rate, usually from 3% to 10%. Morbidity related to the conventional surgery includes myocardial infarction, renal failure, impotence, paralysis, and other conditions. Additionally, even with successful surgery, recovery takes several weeks, and often requires a lengthy hospital stay.

In order to overcome some or all of these drawbacks, endovascular graft placement for the treatment of aneurysms has been proposed. Although very promising, many of the proposed methods and apparatus suffer from other problems. In particular, delivery and placement of the endovascular graft within the vasculature can be problematic. Proper positioning and sizing of the endovascular graft is critical to the successful treatment of an aneurysm. Grafts are often resilient, biased to expand and anchor the graft within the body lumen. These resiliently expanding grafts are tightly compressed within the catheter and impose significant forces against the surrounding catheter bodies, often leading to excess friction between the graft and the catheter wall. These forces complicate the loading of the graft into the catheter, as well as the accurate release of grafts and stents in body lumens. Moreover, the catheters must maneuver the graft within the vascular system. Thus, the catheters are required to have flexible, elongate bodies which are particularly susceptible to the expanding graft, often resulting in invagination of the graft in the soft material of the catheter wall.

For these reasons, it would be desirable to provide improved apparatus and methods for endovascular placement of intraluminal protheses, including grafts, stents, and stent-grafts, for treating aneurysms and other conditions. It would be particularly desirable to provide delivery catheters and methods for the placement of endoluminal tubular prostheses which would facilitate the controlled release of resilient tubular prostheses. It would be particularly desirable to provide delivery catheters and methods which reduce the frictional forces created by the resilient expansion against the catheter during loading and release of the prostheses.

2. Description of the Background Art

Vascular grafts and devices for their endoluminal placement are described in U.S. Pat. Nos. 5,282,824; 5,272,971; 5,242,399; 5,219,355; 5,211,658; 5,201,757; 5,192,297; 5,190,058; 5,158,548; 5,147,370; 5,104,399; 5,092,877; 5,078,726; 5,019,085; 4,990,151; 4,950,227; 4,913,141; 4,886,062; 4,820,298; 4,787,899; 4,617,932; 4,562,596; 4,577,631; and 4,140,126; and European Pat. Publications 539,237; 533,511; 518,839; 518,704; 508 473; 505,686; 466 518; and 461 791. Catheters for placing vascular stents are described in U.S. Pat. Nos. 5,192,297; 5,092,877; 5,089, 005; 5,037,427; 4,969,890; and 4,886,062. Catheters carding a graft structure in a tube or capsule are described in U.S. Pat. Nos. 5,275,622; 5,104,399; and 4,787,899; and EP466518.

SUMMARY OF THE INVENTION

The present invention provides apparatus and methods for the endoluminal placement of intraluminal prostheses, including grafts, stents, and stent-grafts, for the treatment of disease conditions, particularly aneurysms. The intraluminal prostheses will typically comprise a resilient, radially compressible, tubular frame having a proximal end, a distal end, and an axial lumen therebetween. In the case of graft prostheses, a liner, typically a fabric, polymeric sheet, membrane, or the like, will line all or most of the luminal surface of the tubular frame, usually extending from a near-proximal location to a near-distal location. Suitable graft structures for placement using the catheters and methods of the present invention are described in copending application Ser. No. 08/255,681, the full disclosure of which is incorporated herein by reference.

The intraluminal prostheses of the present invention are suitable for a wide variety of therapeutic uses, including stenting of the ureter, urethra, biliary tract, and the like. The present devices and methods will also be useful for the creation of temporary or long term lumens, such as the formation of fistulas. The present invention will find its greatest use, however, in the placement of endovascular prostheses into blood vessels for the treatment of abdominal and other aneurysms, vascular stenoses, and the like.

According to the present invention, a delivery catheter for positioning a radially compressible prosthesis comprises an elongate flexible shaft structure having a proximal end and a distal end. The shaft structure includes a prosthesis receptacle near the distal end. A tubular cover is slidably disposed about the shaft with at least one runner disposed within the distal end of the cover, wherein the runner is formed of a harder material than is the cover. The prosthesis can slide against the hard runner material within the cover in response to a distal force applied from the shaft. Advantageously, the hardness of the runner material avoids invagination of the compressed prosthesis frame in the cover while allowing use of a softer, more flexible cover material to facilitate intraluminal maneuvering of the catheter. Additionally, reduced friction between the prosthesis and cover also facilitates the precise positioning of the prosthesis by reducing the forces input at the proximal end and transmitted through the catheter body. The reduced friction of the present delivery catheter is also beneficial when it is necessary to recapture a partially deployed prothesis.

As used herein, a "prosthesis receptacle" is a structure or region along a shaft in or over which a radially compressible tubular prosthesis is carried during maneuvering of the shaft and prosthesis within a body lumen. The prosthesis receptacle may include a structure or portion at or near the distal end of the shaft which engages the prosthesis to effect its release—for example, a distal force imparting structure on the shaft that restrains proximal movement of the prosthesis as the cover slides proximally. Although the devices and methods of the present invention are illustrated with continuous shafts and covers for clarity, the principles of the present invention are fully compatible with an attachable prosthesis cartridge, as described in parent application Ser. No. 08/255,681, previously incorporated by reference. Similarly, catheter diameters may be reduced proximally of the prosthesis to facilitate intravascular maneuvering within the scope of the present invention Preferably, the present catheter includes a plurality of axially disposed runners affixed together at their proximal ends, thereby reducing contact between the prosthesis and the soft inner surface of the cover. Optionally, the runners remain around the prothesis as the cover slides proximally during deployment. Alternatively, the cover and runners are withdrawn together as the prosthesis slides against the hard runners. Usually, the runners facilitate loading of the prosthesis by compressing the prosthesis as the runners and prosthesis slide together proximally into the cover. The runners are preferably formed of a high strength metal such as stainless steel, a stainless alloy, titanium, a titanium alloy, or a shape memory alloy such as Nitinol™, ideally being 304 or 316 stainless steel.

In a preferred embodiment, the present delivery catheter comprises an elongate flexible shaft and a tubular cover slidably disposed about the shaft. A plurality of elongate runners extend distally from the shaft, the runners having a hardness greater than the cover. The runners are radially constrained when the cover is distally extended over a prosthesis receptacle on the shaft, and are released by proximally retracting the cover. Advantageously, the runners of the present invention can be used to help compress the prosthesis and load it into the cover without damaging the prosthesis frame, either prior to insertion in the patient, or to facilitate recapture of a prosthesis which has been partially deployed within a body lumen.

Preferably, the shaft structure further comprises a core shaft with a guidewire lumen, the core shaft and cover providing an atraumatic distal tip to avoid injury during insertion. Optionally, the core shaft is attached to the shaft. Preferably, the core shaft can slide independently of the shaft, allowing retraction of a distal nosecone through the prosthesis prior to withdrawing the runners. This reduces the possibility of moving a partially deployed prosthesis by allowing manipulation of the nosecone within the prosthesis, rather than withdrawing both the nosecone and the surrounding runners simultaneously.

Optionally, the present catheter further includes a housing at the proximal end of the shaft with a mechanical advantage mechanism, preferably a linear screw, which further reduces the actuation forces and allows precise, gradual release of the prosthesis. A friction reducer tube may further be provided to facilitate withdrawing of the cover through an introducer sheath. The friction reducer tube is slidably disposed over the cover of the delivery catheter of the present invention, and includes a seal against the cover to provide hemostasis. The friction reducer tube is insertable within an introduction sheath, and allows movement of the delivery catheter with less friction than the introduction sheath, which must seal against a variety of invasive surgical devices. Optionally, a brace mechanically couples the proximal end of the shaft to the introduction sheath to prevent distal movement of the prosthesis or runners during deployment. Such a brace is particularly advantageous when a single surgeon is to manipulate the delivery catheter of the present invention.

The runners are again preferably formed of a high strength alloy. There are preferably between 1 and 20 runners, each runner being a strip which is longer than the prosthesis. The total width of all the runners is limited by the internal diameter of the cover, as the runners are usually affixed about the shaft side to side, and the runner/shaft assembly must slide within the cover. The runners will often be narrower than this, however, to allow the expanded prosthesis to anchor to the inner surface of the body lumen between the runners. The runners are each preferably in the range from 0.01 to 0.09 inch wide, and preferably between 0.001 and 0.02 inch thick.

In another aspect, the present invention provides an improved orientation indicating catheter for placement of an asymmetric prosthesis in a branching body lumen. The present orientation indicating catheter comprises an asymmetric marker, on the shaft structure which indicates the rotational orientation of the prosthesis. Preferably, a branch axial marker on the shaft structure indicates the axial location of the prosthesis branch. These rotational and axial indicators prevent placement of the prosthesis branch below the branching body lumen, or crossing of the branches, either of which could reduce or even completely block flow through one branch of the body lumen system. Similarly, a position indicating catheter having a safety marker prevents placement of a secondary prosthesis too far within the branch of a branching prosthesis, reducing the danger of the tubular prosthesis folding over and blocking flow.

In yet another aspect, the present invention provides an expandable tip catheter for placement of a radially compressible prosthesis having a large diameter portion and a small diameter end, the catheter comprising an elongate shaft structure having a prosthesis receptacle near a distal end, and a cover slidably disposed about the shaft structure. The cover comprises a body portion and a resilient structure extending from the distal end of the body portion. The catheter restrains the prosthesis with the small diameter end of the prosthesis in the distal resilient structure of the cover, allowing the distal end of the catheter to have a smaller outer diameter than the body. Advantageously, the distal end may be advanced into a smaller body lumen branch, and the expandable structure can expand over a large diameter end of the prosthesis as the cover is retracted into a larger body lumen. The resilient structure preferably comprises a braided mesh tubing with an elastomeric material disposed over the mesh tubing. Alternatively, the resilient structure comprises a sheath having one or more axial slits, or a rolled or folded pliable material.

According to the method of the present invention, a resilient, radially compressible prosthesis is loaded into a tubular cover by compressing the prosthesis between a plurality of elongate runners and sliding the runners into the cover. The cover may then be positioned within a body lumen so the prosthesis is at a target location, and deployed by withdrawing the cover relative to the prosthesis. Optionally, the runners exit the cover distally with the prosthesis, and are retracted after the cover. Alternatively, the runners and cover are retracted together.

DESCRIPTION OF THE PREFERRED EMBODIMENT

The present invention provides apparatus and methods for the endoluminal placement of intraluminal tubular prostheses, particularly grafts, stents, and stent-grafts. The tubular prostheses will be radially compressible, and the apparatus of the present invention will maintain the prostheses under compression in a narrow-diameter configuration while they are being introduced to the body lumen, typically during surgical cutdown or percutaneous introduction procedures. Placement of the tubular prosthesis is effected by releasing the prosthesis at a target location in the lumen. Thus, it is necessary that the prosthesis be sufficiently resilient and conformable to expand against the interior wall of the body lumen. It will be appreciated, however, that the prosthesis may be formed at least partly from malleable components which permit it to be subsequently further expanded, typically by inflation of a balloon within the lumen of the prosthesis.

Figure 1:
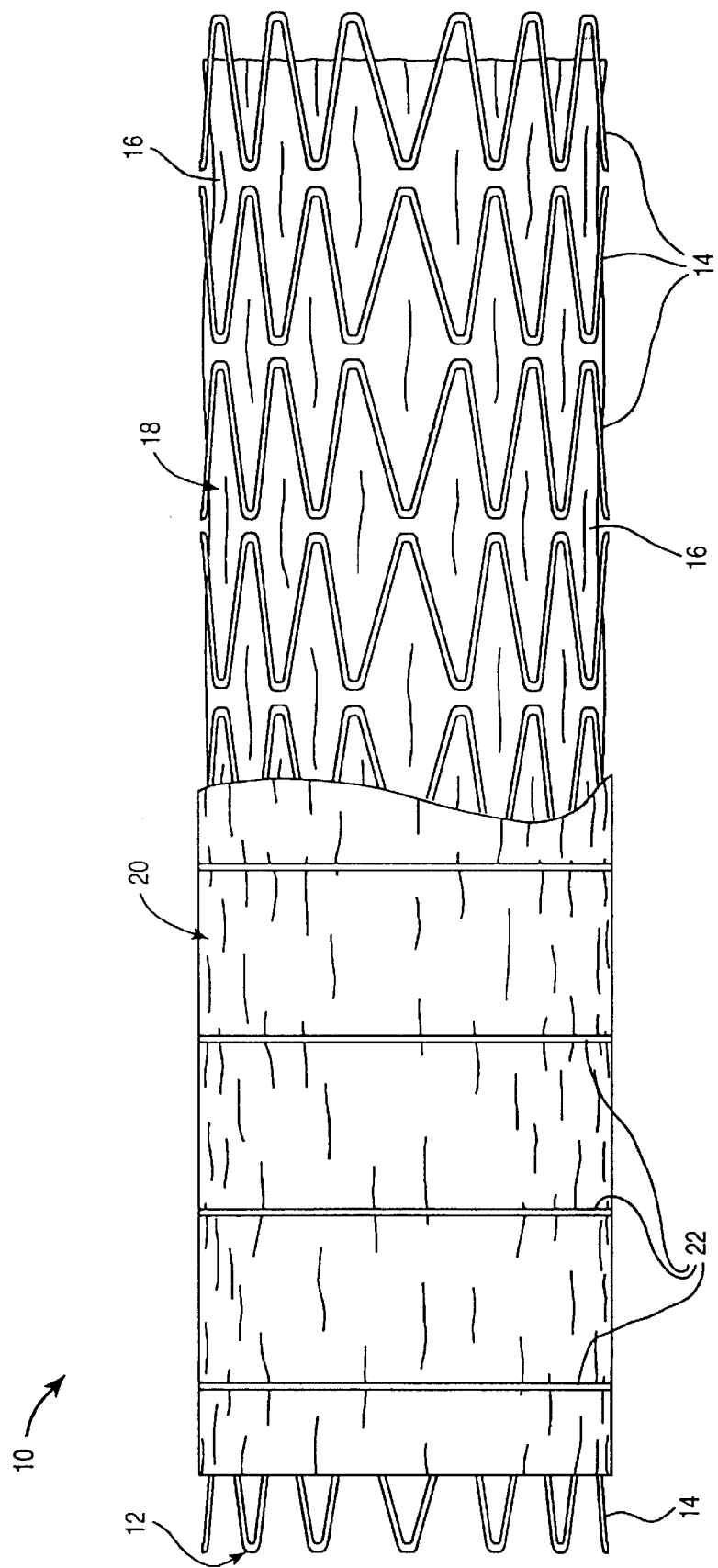
FIG. 1 is a side view of a vascular graft which is exemplary of the type of radially compressible tubular prosthesis which may be placed using the delivery catheter of the present invention.

The present invention will find greatest use in the percutaneous placement of endovascular prostheses for the treatment of diseases of the vasculature, particularly aneurysms, stenoses, and the like. Suitable prosthesis structures which may be deployed by the delivery catheter of the present invention are described in copending application Ser. No. 08/255,681, the full disclosure of which is incorporated herein by reference. One exemplary graft structure 10 is illustrated in FIG. 1. Prosthesis 10 comprises a perforate tubular frame 12 which includes a plurality of independent (non-connected) band members 14 separated from each other by small gaps 16. The tubular frame 12 is covered by an inner liner 18 and an outer liner 20, where the inner and outer liners together encase or sandwich the otherwise free-floating band members 14 therebetween. In order to secure the band members 14 in place, and secure the liners to the perforate tubular frame 12, the inner and outer liners are joined together along circumferential lines 22, preferably aligned with the gaps 16 between adjacent band members 14. The liners may be joined together by stitching, heat welding, ultrasonic welding, or the like. In the exemplary embodiment, the liners 18 and 20 are formed from polymeric sheet material and are joined together by ultrasonic welding. The band members 14 at each end of the graft 10 will have to be further secured to the liners 18 and 20. For example, they could be stitched, welded, or otherwise joined to the liners to hold them in place. The graft 10 will typically have a length in the range from about 50 mm to 500 mm, preferably from 80 mm to 200 mm, with a relaxed diameter in the range from about 4 mm to 45 mm, preferably being in the range from 5 mm to 25 mm. Such graft structures will be particularly suitable for treating vascular aneurysms.

In connection with the present invention, it has been discovered that the placement of resilient tubular prostheses imposes serious demands on delivery and imaging systems, as well as on the attending medical personnel. Prostheses are highly compressed within delivery catheters to allow maneuvering within the vascular system. The compressive forces have been found to lead to excessive friction during deployment from the delivery catheters of the prior art. Additionally, visualization of compressed prostheses within the catheter is problematic, particularly when a branched prosthesis must be placed in a branching body lumen in a specific orientation.

The delivery catheters of the present invention facilitate deployment of resilient prostheses by reducing friction at the prosthesis/catheter interface, avoiding any increase in the stiffness of the delivery system where it is not needed. In connection with the present invention, it has been discovered that compressed prostheses are largely rigid, which reduces any penalty in flexibility imposed by including hard, friction-reducing runners around the prosthesis.

Figure 2:
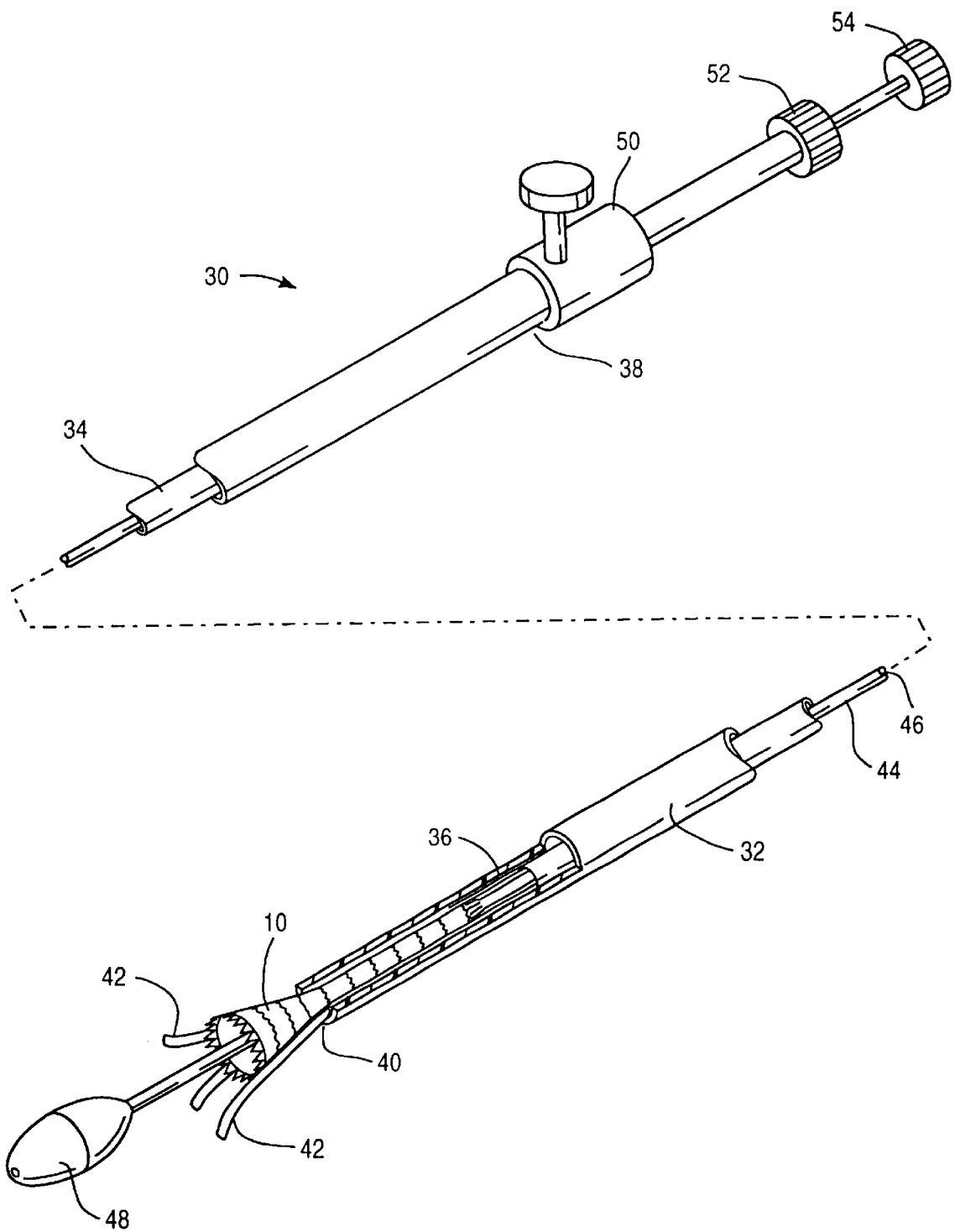
FIG. 2 is a perspective view of a first embodiment of a delivery catheter of the present invention, with a portion of the distal end broken away to disclose a prosthesis therein.

Referring now to FIG. 2, a delivery catheter 30 constructed in accordance with the principles of the present invention comprises a tubular cover 32 and a shaft or inner catheter body 34. Cover 32 has a central lumen 36 extending from a proximal end 38 to a distal end 40. Shaft 34 is slidably received within central lumen 36 and extends proximally of the proximal end of cover 32.

A plurality of runners 42 extend distally from the distal end of shaft 34. Runners 42 line a portion of the inner surface of lumen 36, and slide within the lumen with the shaft. Shaft 34 also has a lumen, in which a core shaft 44 is slidably disposed. Core shaft 44 has a guidewire lumen 46. Guidewire lumen 46 optionally receives an intravascular ultrasound (IVUS) imaging transducer to provide imaging prior to, during, and after deployment of the prosthesis. Nosecone 48 is fixed to the distal end of core shaft 44, and can therefore move independently of runners 42.

Graft 10 is radially compressed and restrained within the plurality of runners 42. In turn, cover 32 prevents runners 42 from expanding outward. Runners 42 are formed from a hard material, and distribute the expansion load of prosthesis 10 over the inner surface of central lumen 36. Advantageously, the prosthesis does not invaginate in the lumen surface, and is thus able to slide relative to the cover in response to a moderate distal force. In the embodiment of FIG. 2, the deploying force is applied proximally against a slider 50 attached to distal end 38 of cover 32, while holding a lure fitting 52 at the distal end of shaft 34. An additional lure adaptor 54 at the distal end of core shaft 44 allows the core shaft to be releasably secured to the shaft 34.

Figure 3:
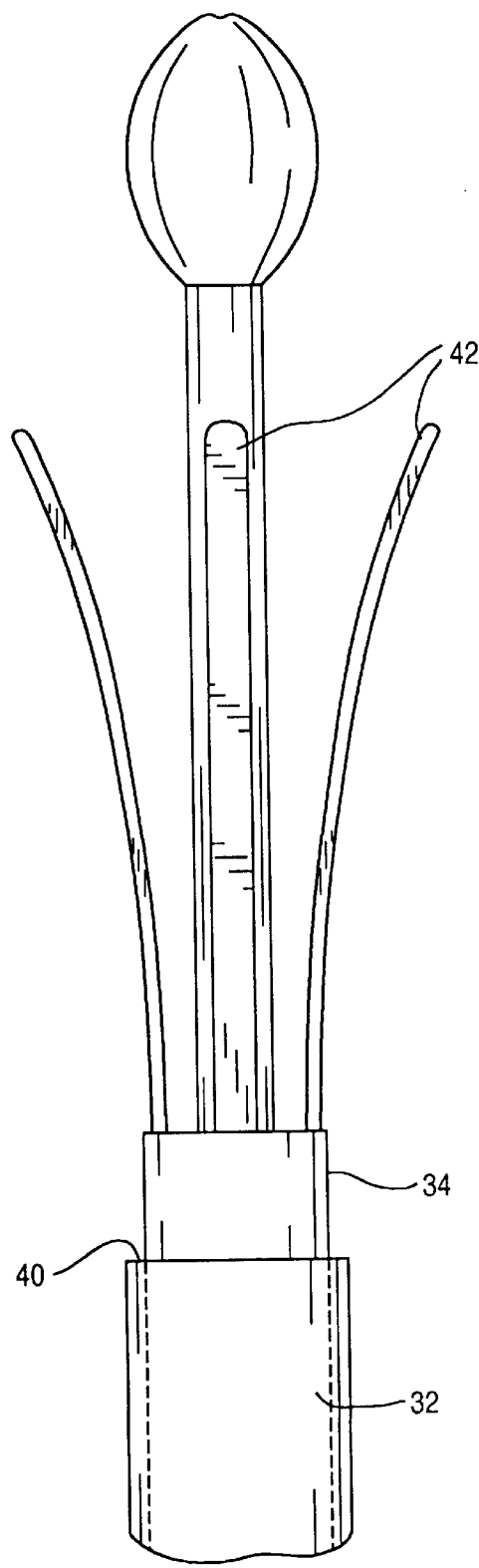
FIGS. 3 and 4 illustrate the loading of a graft into the delivery catheter of FIG. 2.
Figure 4:
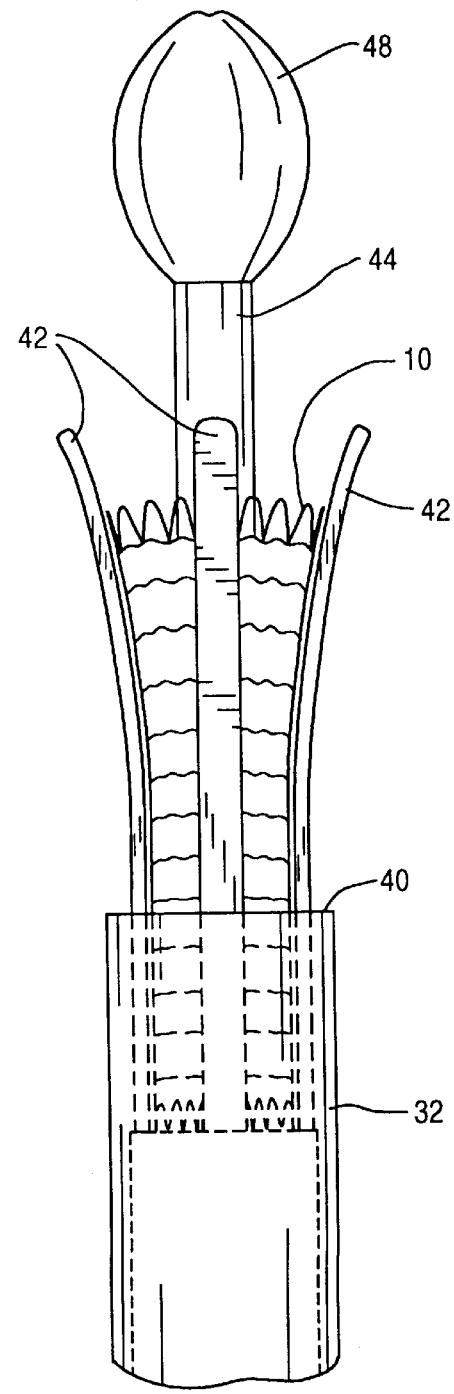
Figure 5:
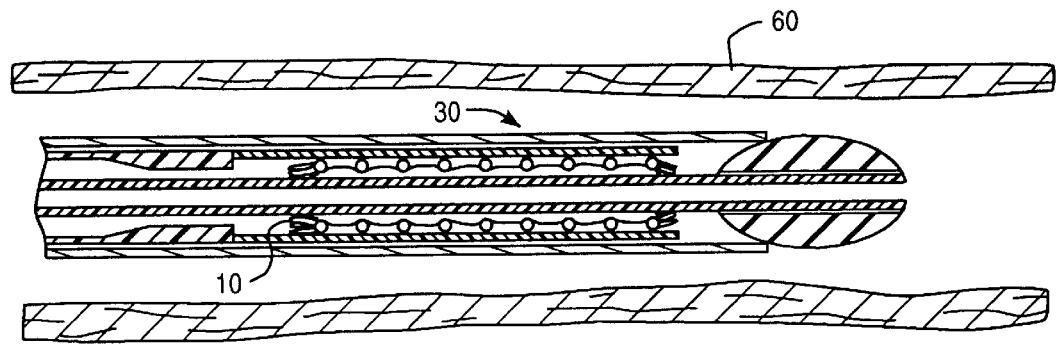
FIGS. 5–7 illustrate the use of the delivery catheter of FIG. 2 in placement of a radially compressible tubular prosthesis in a body lumen.

Referring now to FIGS. 3 and 4, loading of graft 10 into the distal end 40 of cover 32 is facilitated by use of runners 42. As seen in FIG. 3, extending shaft 34 distally allows runners 42 to flex outward. Graft 10 may be inserted between the outward flexed runners and compressed by withdrawing runners 42 and shaft 34 into the distal end 40 of cover 32. Nosecone 48 and core shaft 44 are shown attached to shaft 34 during loading. Alternatively, nosecone 48 may be attached to core shaft 44 after the loading of prosthesis 10. Prosthesis 10 is preferably formed of a heat memory alloy such as Nitinol™. To maintain graft 10 in a compressed state, the loading process may be done in a cold environment, such as that provided by a cold spray, liquid nitrogen, freon, an air vortex, or the like.

Figure 6:
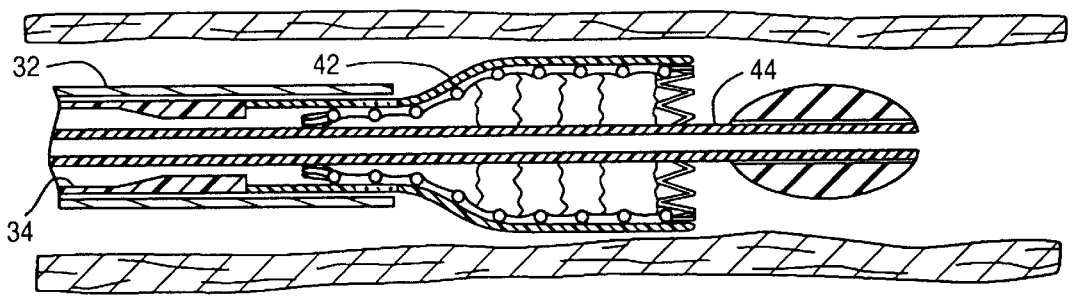
Figure 7:
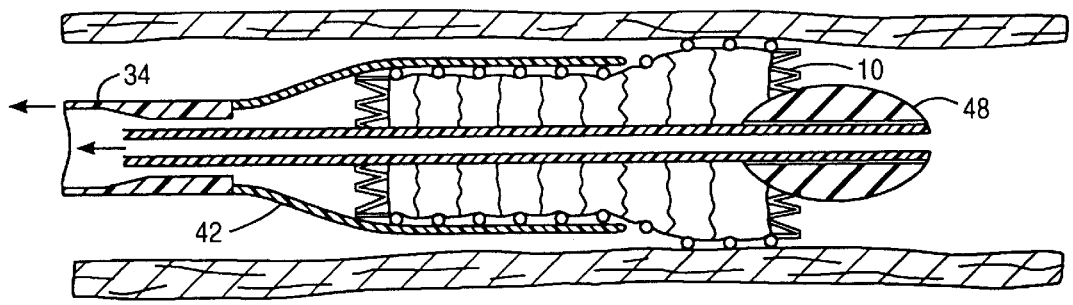
Figure 8:
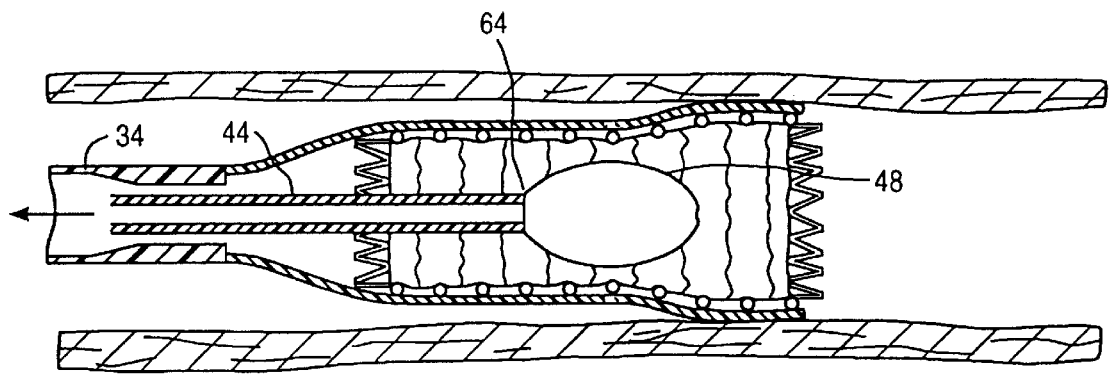
FIG. 8 illustrates a preferred method of use of the delivery catheter of FIG. 2, in which tapered nosecone is withdrawn independently of the runners.

Referring now to FIGS. 5 through 8, placement of graft 10 within a body lumen 60 begins by positioning catheter 30 at a target location. As illustrated in FIG. 6, graft 10 is allowed to expand by retracting cover 32 proximally relative to shaft 34 and core shaft 44. As cover 32 is retracted, runners 42 maintain their axial position, sliding over the inner surface of cover 32. Once the graft 10 has fully expanded within body lumen 60, it is axially anchored by expansion against the lumen wall between the runners. Runners 32 may then be retracted proximally with shaft 34 and nosecone 48. The hard surface of runner 32 allows shaft 34 to be retracted smoothly, with little possibility of dragging graft 10 from the target position. The graft cover may also help to reduce friction during deployment. The possibility of dragging the prosthesis is further reduced by retracting nosecone 48 having a tapered proximal end 64 independently from shaft 34, as illustrated in FIG. 8. Finally, it will be recognized that the runners may also be used to help recapture a partially-deployed prosthesis.

Figure 9:
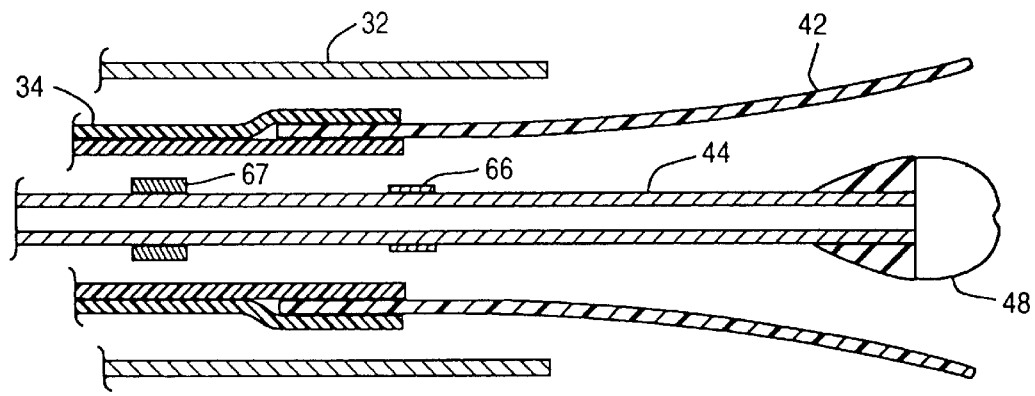
FIG. 9 is an exploded cross-sectional view of the delivery catheter of FIG. 2.

Referring now to FIG. 9, the elements of the present graft delivery catheter will be described. Cover 32 must be strong enough to withstand the expansion force of graft 10 but must also be flexible to allow intravascular atraumatic maneuvering. Cover 32 is optionally formed of a high strength thermoplastic elastomer such as Hytrel™. Alternatively, cover 32 may be formed of a braided reinforced polymer tubing or a linear reinforced tubing, preferably having fibers of a polyamide such as Kevlar™, Spectra™, or the like, embedded to improve tensile strength without reducing flexibility. Preferably, the cover includes a radiopaque contrast medium, e.g., a $B_4SO_4$ compound, to allow imaging of the placement of catheter 30 within a body lumen using fluoroscopy. Shaft 34 is preferably formed from PEEK, nylon, or the like, to provide column strength. Runners 42 are formed from a high strength biocompatible alloy such as Nitinol™, stainless steel, or a stainless steel alloy. Runners 42 are bonded to shaft 34, preferably being laminated between inner and outer layers of nylon, a thermoplastic elastomer such as Pebax™, or the like. Core shaft 44 is also preferably formed of PEEK. Nosecone 48 may be formed of stainless steel and bonded to the distal end of core shaft 44, or may alternatively be molded of a radiopaque plastic comprising Pebax™, nylon, Hytrel™, or the like. In any case, nosecone 48 preferably includes a radiopaque element, thereby giving an indication of the location of the distal end of graft 10 during fluoroscopically guided prostheses placement. In certain embodiments, core shaft 44 further supports marker ring 66, comprising platinum, barium, or the like, to provide a sharp radiographic contrast. Optionally, distal force imparting structure 67 is bonded to the core shaft to slide the compressed prosthesis distally over the runners.

Figure 9A:
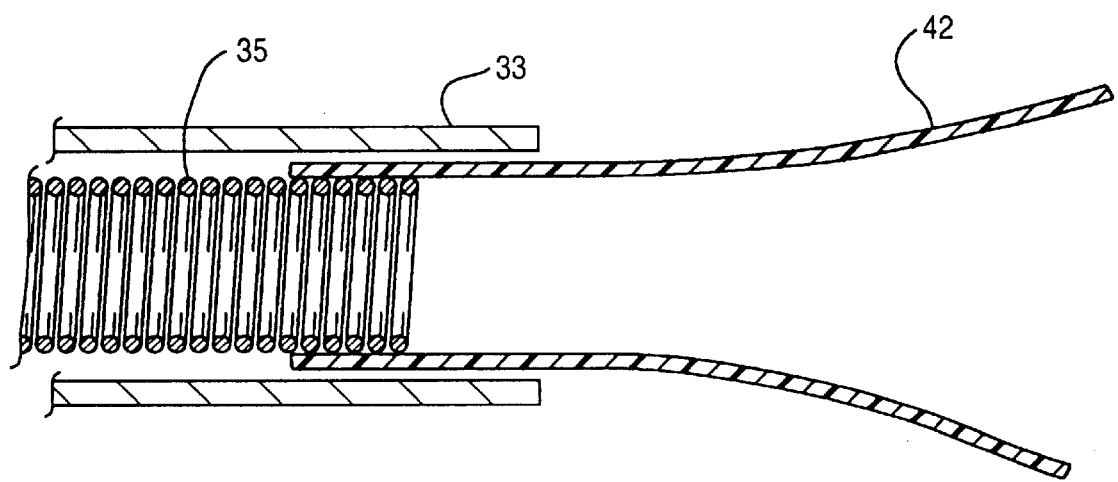
FIG. 9A is a cross-section of an alternative shaft structure and cover having increased flexibility.

Referring now to FIG. 9A, a helical shaft 35 provides high column strength with flexibility. Helical shaft 35 is formed from a tightly wound, high strength metal, preferably comprising stainless steel. Helical shaft 35 is easily welded to runners 42, where similar metals are used for both. Alternatively, runners 42 are laminated to helical shaft 35 with inner and/or outer layers of nylon, Pebax™, or the like. A composite cover 33 comprising polymer reinforced tubing having braided or linear Kevlar™, Spectra™, or the like, further enhances flexibility of the delivery catheter of the present invention.

Figure 10:
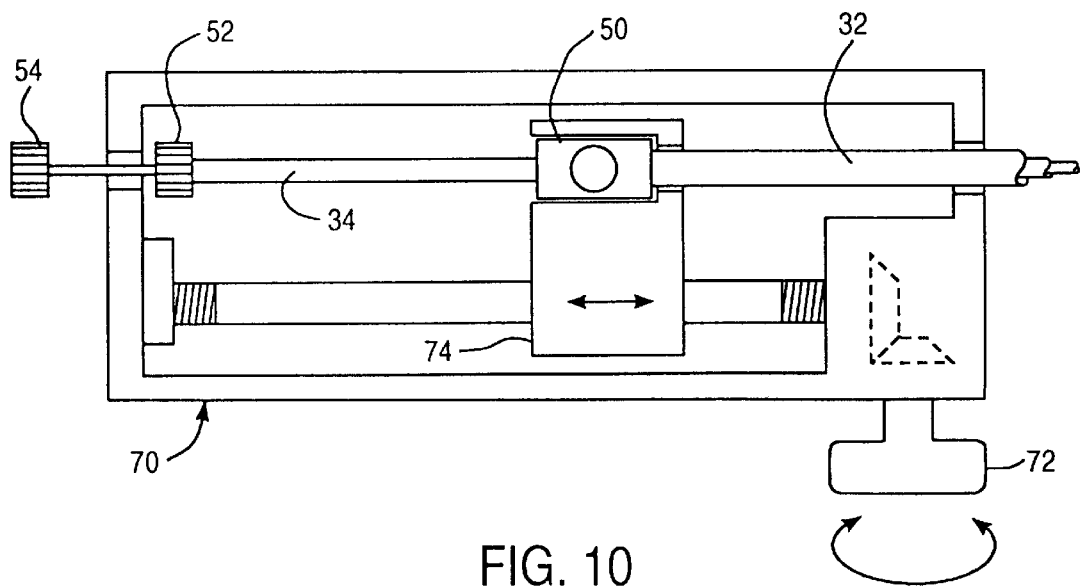
FIG. 10 illustrates a housing at the proximal end of the delivery catheter of FIG. 2 which provides a mechanical advantage for withdrawing the cover.

The delivery catheters of the present invention significantly reduce the force required to deploy a prosthesis within a body lumen. Nonetheless, the force required to withdraw cover 32 remains substantial. For this reason, the present invention further provides a housing 70 to be attached to the distal end of shaft 34, as illustrated in FIG. 10. Rotation of handle 72 moves follower 74 along a linear screw. Slider 50 at the proximal end of cover 32 is driven axially by the movement of the follower. Cover 32 is withdrawn during deployment of the prosthesis by articulating handle 72 so as to drive slider 50 toward lure fitting 52 at the proximal end of shaft 34. The force required to withdraw the cover is typically on the order of 1 to 10 lbs., requiring only a modest mechanical advantage. However, a mechanical advantage ratio in the range from 5 to 50, as measured from the linear travel at the outside edge of handle 72 to the linear motion of follower 74, provides a highly controlled deployment. Clearly, a wide variety of mechanical linkages are available to provide such a mechanical advantage. It is particularly advantageous to provide a mechanism which allows manipulation with a single hand, as this leaves the alternate hand free to manipulate the cover relative to an introducer sheath. It will be noted that housing 70 allows independent manipulation of core shaft 44 using second lure fitting 54, as described above regarding FIG. 8.

Figure 11:
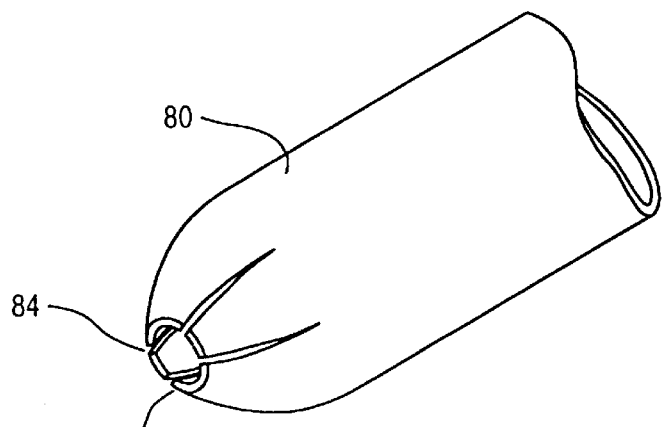
FIG. 11 illustrates a delivery catheter cover having a rounded, atraumatic distal end with a split tip.

Referring now to FIG. 11, an alternative cover 80 provides an atraumatic distal end 82 with a reduced nosecone diameter, or, alternatively, no nosecone at the distal end of core shaft 44. Atraumatic cover 80 includes a series of splits 84 to allow the distal tip of atraumatic cover 80 to open during deployment of prosthesis 10.

Figure 12:
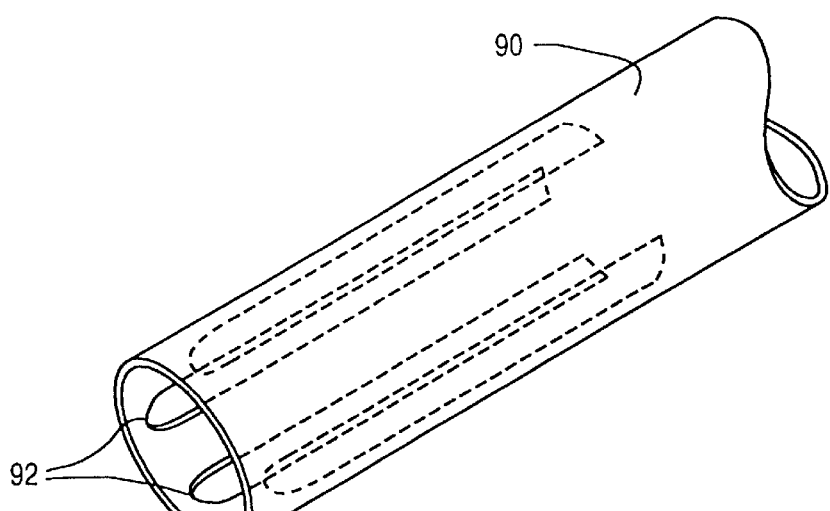
FIG. 12 illustrates a delivery catheter cover having runners imbedded within the distal end.

Referring now to FIG. 12, a further alternative cover 90, having runners 92 embedded within the central lumen, will also reduce the friction between the prosthesis and the cover during prosthesis placement. Furthermore, such a structure eliminates any danger of injury to the walls of a body lumen during placement by a distal movement of the exposed runners. Moreover, similar safety advantages could be obtained using the delivery catheter of FIG. 2 by retaining runners 42 within cover 32 during deployment of prosthesis 10. An alternative structure must be provided to apply a distal force against the prosthesis, such as distal force imparting structure 67 shown in FIG. 9.

Figure 13:
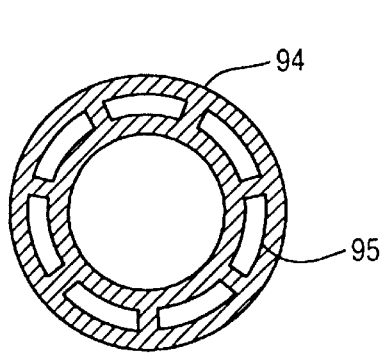
FIGS. 13 and 14 are alternative cross-sectional views of a delivery catheter cover.
Figure 14:
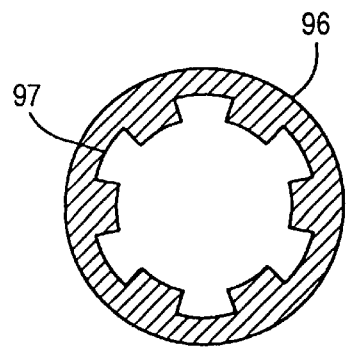

Referring now to FIGS. 13 and 14, alternative cross sections 94 and 96 for a delivery catheter tubular cover or shaft will provide additional column strength without a corresponding increase in stiffness. Slots 95 are also suitable for receiving the runners, thus forming the runner/shaft laminated bond. Indents 97 may receive the free distal portion of the runners to prevent rotation of the prosthesis relative to the cover during manipulation of the shaft. Alternatively, a smooth cover lumen facilitates such rotation by allowing the runners to slidingly rotate against the cover lumen surface.

Figure 15:
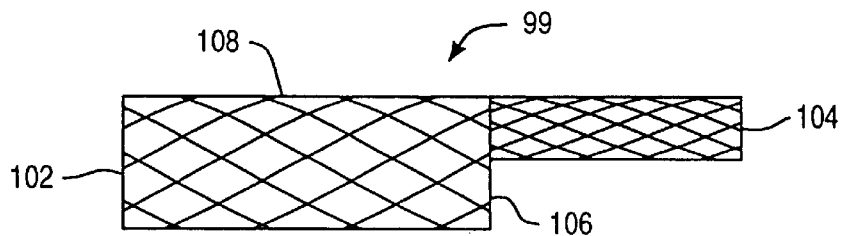
FIG. 15 is a side view of a vascular graft which is exemplary of the branching, resilient, radially compressible prostheses which may be placed in branching body lumens using the delivery catheters of the present invention.

A second exemplary prosthesis structure for use with the delivery catheter of the present invention is illustrated in FIG. 15. Branched prostheses are particularly useful for treatment of aortic aneurysms which extend distally into one or both of the iliac arteries. Branched prosthesis 99 has a large diameter end 102 and a small diameter end 104. Large diameter end 102 features a large common lumen which is in open communication with a first branched lumen of small diameter end 104. The common lumen is further opened at branch 106. Branched prosthesis 99 is formed of a perforate tubular member similar to that used in graft 10. Branched prosthesis 99 may further include a liner as described above.

Treatment of aortic aneurysms using branched prostheses requires placement of the large diameter end in the abdominal aorta with the small diameter end extending into one of the iliac arteries. It will further be understood that it is critical to have branch 106 correctly oriented toward the alternate iliac artery for proper blood flow, whether or not a second tubular prosthesis is placed within open branch 106 and extending into the alternate iliac artery.

Figure 16:
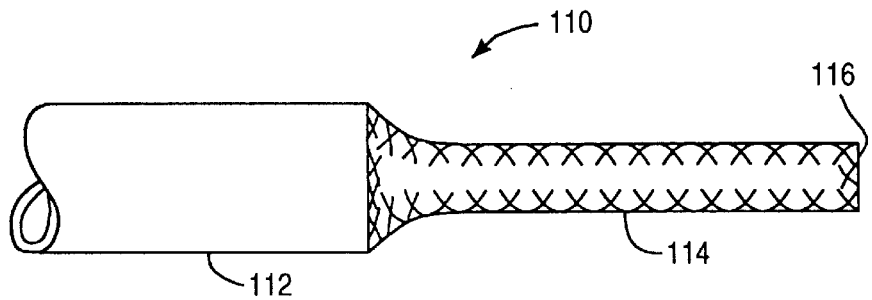
FIGS. 16 and 17 illustrate a preferred embodiment of an alternate embodiment of the present delivery catheter having a cover with an expandable distal structure for use with the branched stent of FIG. 15.
Figure 17:
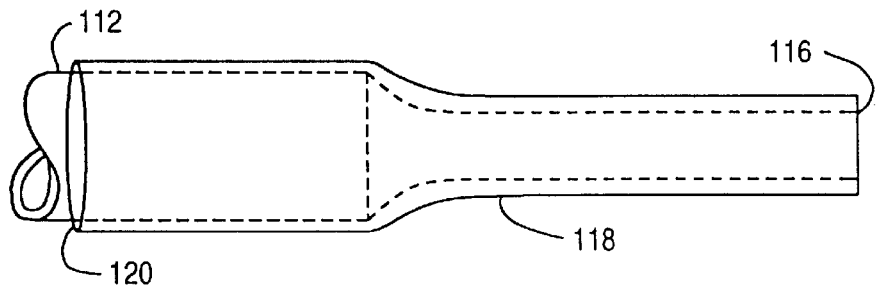

Referring now to FIGS. 16 and 17, an exemplary expandable cover 110 for use with branched prostheses comprises a tube 112 and a radially expandable cylindrical structure 114 extending distally of body 112. Body 112 is formed of material similar to that used for cover 32 of the delivery catheter of FIG. 2. Expandable structure 114 comprises a braided, expandable mesh tubing which is bonded or molded into body 112. The mesh tubing expands easily, and is unable to radially compress branched graft 100, but provides a relatively hard surface against which the branched prosthesis can slide distally during deployment. An elastomeric outer coating 118 is disposed over the entire length of the expandable structure and extends proximally onto body 112. Elastomeric outer coating 118 comprises rubber, latex, silicone, polyurethane, a thermoplastic urethane such as C-FLEX™, or the like, and provides the radial compression which retains branched graft 100 in a radially compressed mode.

Figure 19:
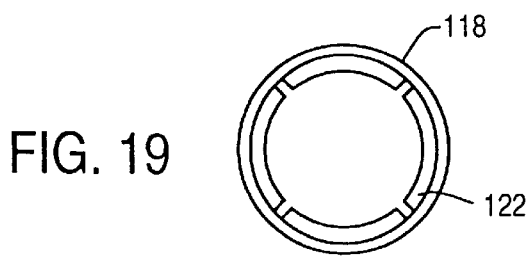
FIGS. 18–21 are alternative cross-sectional views of the expandable structure of the delivery catheter of FIGS. 16–17.
Figure 18:
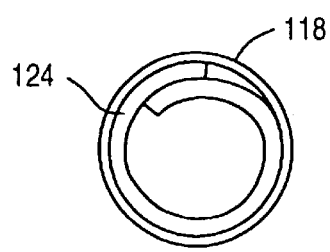
Figure 20:
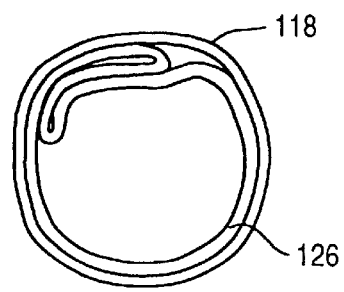
Figure 21:
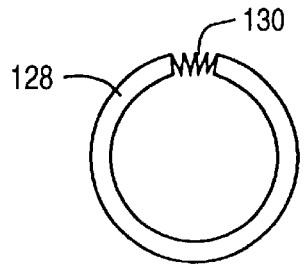

Referring now to FIGS. 19 to 21, alternative radially expandable cylindrical structures may be formed by extending the material of body 112, and cutting a series of slits to form extended arms 122. Alternatively, a single slit may be used, and the material may be overlapped to form a coil 124. In a still further alternative, a pliable material may be folded over and extended from body 112 to form a folded tube 126. Folded tube 126 is preferably formed of a low friction, pliable material such as PTFE or the like. In yet another alternative structure, open tube 128 having a biasing means 130, such as a metal spring or an elastomeric material, may also be used.

Figure 22:
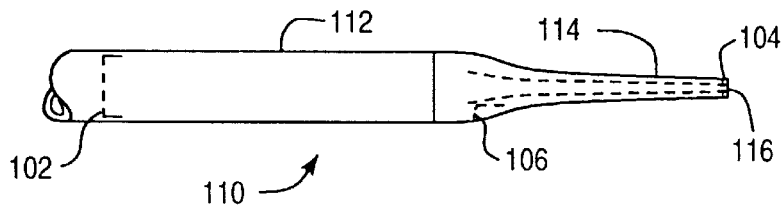
FIGS. 22–24 illustrate the use of the alternative delivery catheter of FIGS. 16–17.
Figure 23:
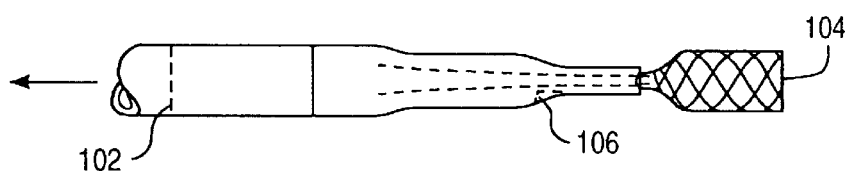
Figure 24:
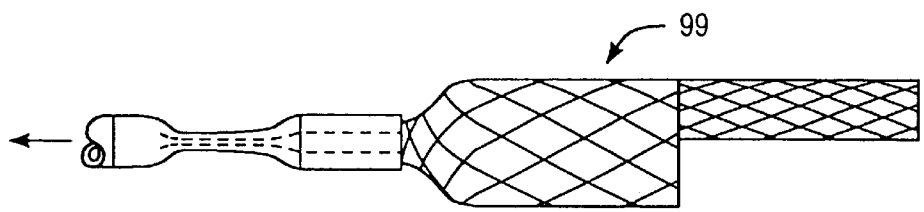

The use of expandable cover 110 will be described with reference to FIGS. 22–24. Branched prosthesis 99 is loaded into expandable cover 110 with a small diameter end 104 of the prosthesis in a distal expandable structure 114. Large diameter end 102 of branched prosthesis 99 is radially restrained within body 112. The outer diameter of expandable structure 114 is less than the outer diameter of body 112, advantageously allowing the distal end of the delivery catheter to extend into the narrower iliac arteries during a superior placement. Once branched prosthesis 99 is properly positioned at a target location within the delivery catheter, expandable cover 110 may be withdrawn proximally. Expandable structure 114 expands to pass the large diameter end 102 as branch 106 slides distally. Large diameter end 102 and body 112 which restrains it need never enter the restricted diameter of the iliac artery. Similarly, the present expandable cover will be useful for placement of any prosthesis having a distal taper, a smaller distal segment, or a small end and a large portion along its axis.

Figure 25:
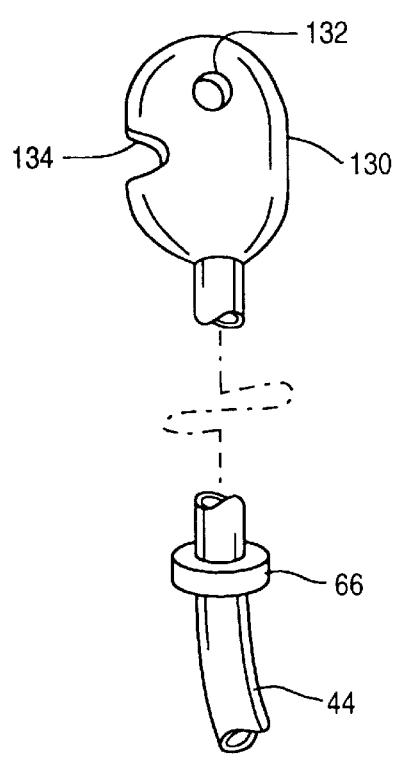
FIG. 25 illustrates a core shaft having a preferred nosecone for use with the delivery catheters of the present invention to rotationally and axially position branching prostheses within branching body lumens under imaging.
Figure 26:
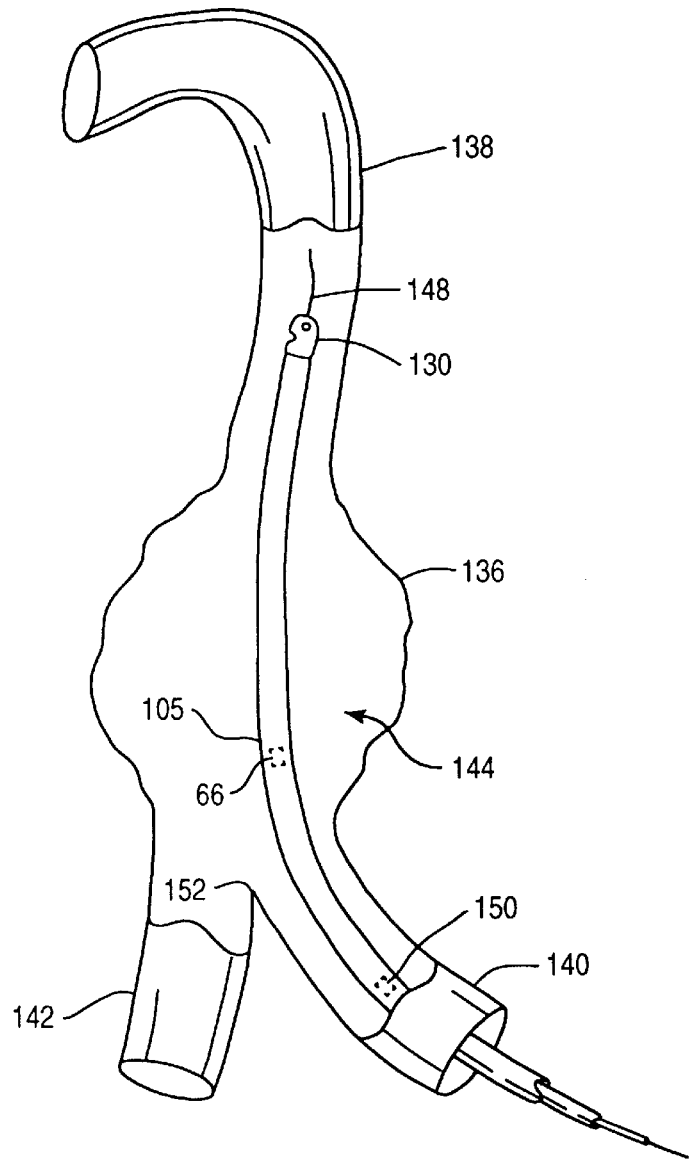
FIGS. 26–30 illustrate the use of a delivery catheter having the preferred shaft of FIG. 25 in placement of a branched prosthesis within a branching body lumen.

Referring now to FIG. 25, an alternative embodiment of the present nosecone which is particularly useful during the orientation of branched prostheses will be described. An orientation indicating nosecone 130 comprises a stainless steel or other radiopaque structure having a hole 132 and a notch 134. When imaged using fluoroscopy, radiography, or other known imaging modalities, orientation indicating nosecone 130 will provide an indication of the orientation of a branch prior to deployment of a branched prosthesis or stent. For an inferior approach, marker ring 66 is a predetermined distance proximal of a branch 105 when a branched graft 100 is radially restrained within the delivery catheter (see FIG. 26), thus providing a branch axial marker. A wide variety of asymmetric radiopaque shapes and markers may be used with the present delivery catheter system. It is preferable that the markers remain in position during withdrawal of the cover, and that the markers clearly identify the orientation of a branch 105. It is particularly prefered that marker ring 66 be toward the branch end from branch 105 to ensure the branch is not placed within the iliac artery.

Referring now to FIGS. 26–30, a method of placement of a branched prosthesis within an aortic aneurysm using the present delivery catheter having the orientation indicating nosecone 130 will be described in regard to branched graft 100. An aneurysm 136 located on an abdominal aorta 138 in close proximity to first and second iliacs 140, 142 is to be treated with a branched graft. A delivery catheter 144 having orientation indicating nosecone 130 is positioned from an inferior placement using a guidewire 148. The axial position and length of branched graft 100 is indicated by orientation indicating nosecone 130 and by a proximal indicator 150, which is structurally similar to marker ring 66, and is affixed to the core shaft adjacent to the proximal end of the prosthesis. Marker ring 66 is used as a branch axial indicator, and is placed distally of the body lumen branch 152 to ensure that the branch of branching graft 100 remains within the common lumen. Furthermore, the rotational orientation of the graft is indicated by notch 134 on orientation indicating nosecone 130. The precise rotational orientation may be determined by lining up hole 132 with the imaging energy stream, such that the image of hole 132 and notch 134 are radiographically clear.

Figure 27:
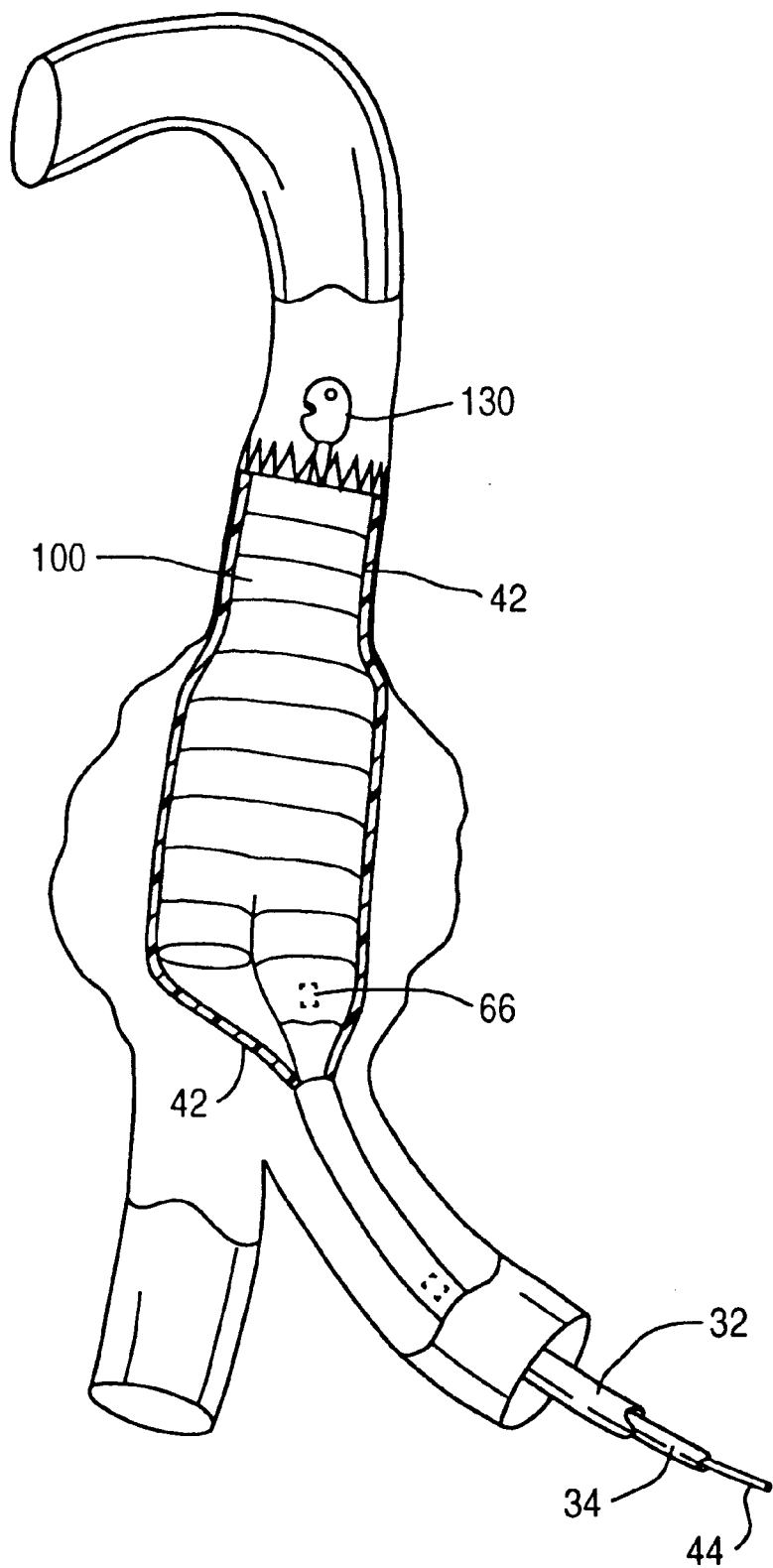
Figure 28:
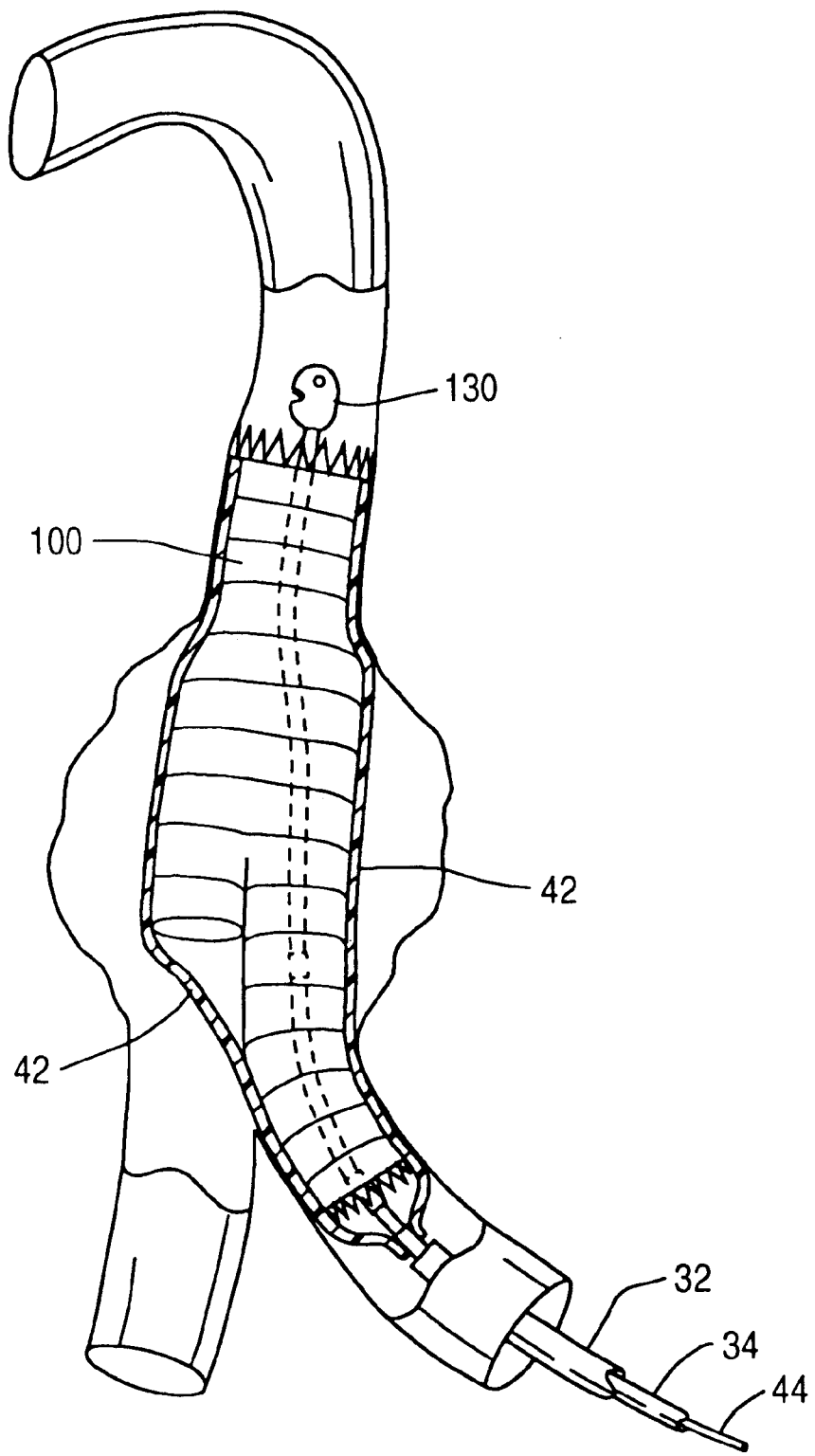

Once delivery catheter 144 is properly positioned, the cover 32 may be withdrawn proximally as illustrated in FIG. 27. Shaft 34 and core shaft 44 remain at the target position, allowing runners 42 to slide over the central lumen 36 of cover 32. Additionally, orientation indicating nosecone 130 and marker ring 66 remain at the axial location of branched graft 100. Alternatively, the cover 32 may be withdrawn a little at a time, with the runners withdrawn back simultaneously into the cover each time. In a still further alternative, runners 42 may remain within cover 32, and branched graft 100 may be held at the target position by a force imparting structure attached to core shaft 44. Such force imparting structures are more fully explained in application Ser. No. 08/294,021, previously incorporated herein by reference. Optionally, core shaft 44 remains stationary while withdrawing the runners so that nosecone 130 does not drag branched prosthesis 100 from the target location.

Figure 29:
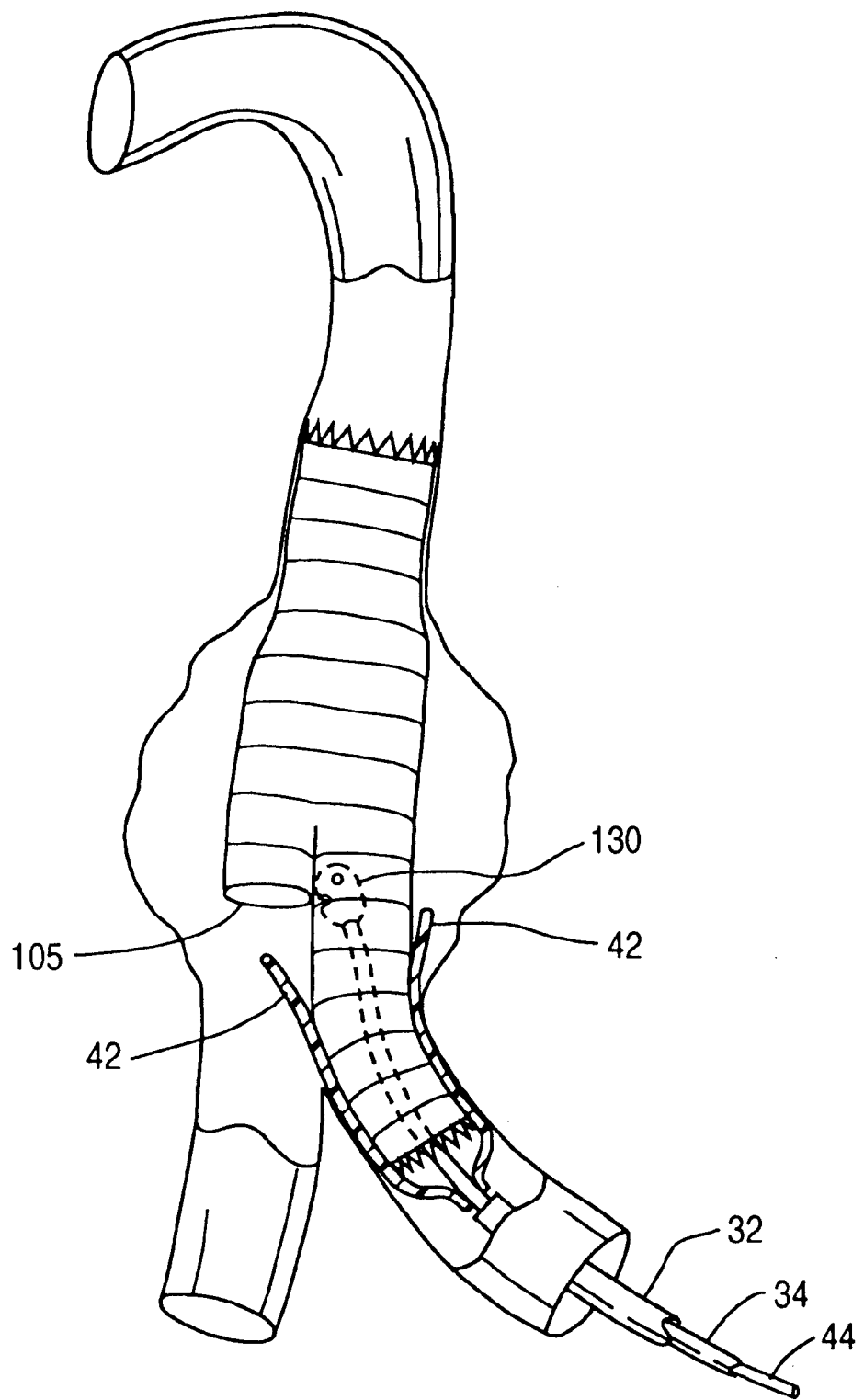

Referring now to FIG. 29, once cover 32 has been withdrawn, runners 42 and nosecone 130 are withdrawn simultaneously through the branched prosthesis. Core shaft 44 and shaft 34, which are optionally attached, are withdrawn proximally. The runners may be withdrawn into cover 32, or the delivery catheter may move proximally with the runners remaining exposed. Alternatively, core shaft 44 is withdrawn independently of shaft 34 in a proximal direction. Very little force should be required to withdraw nosecone 130 independently of runners 42. Any friction which is encountered indicates that nosecone 130 may be snagged, for example, on branch 105. The surgeon may then manipulate core shaft 44 to free nosecone 130, and thereby overcome such a snag. Once orientation indicating nosecone 130 is fully withdrawn shaft 34 and runners 42 may be retracted, leaving branched graft 100 in place. graft 100 in place.

Figure 30:
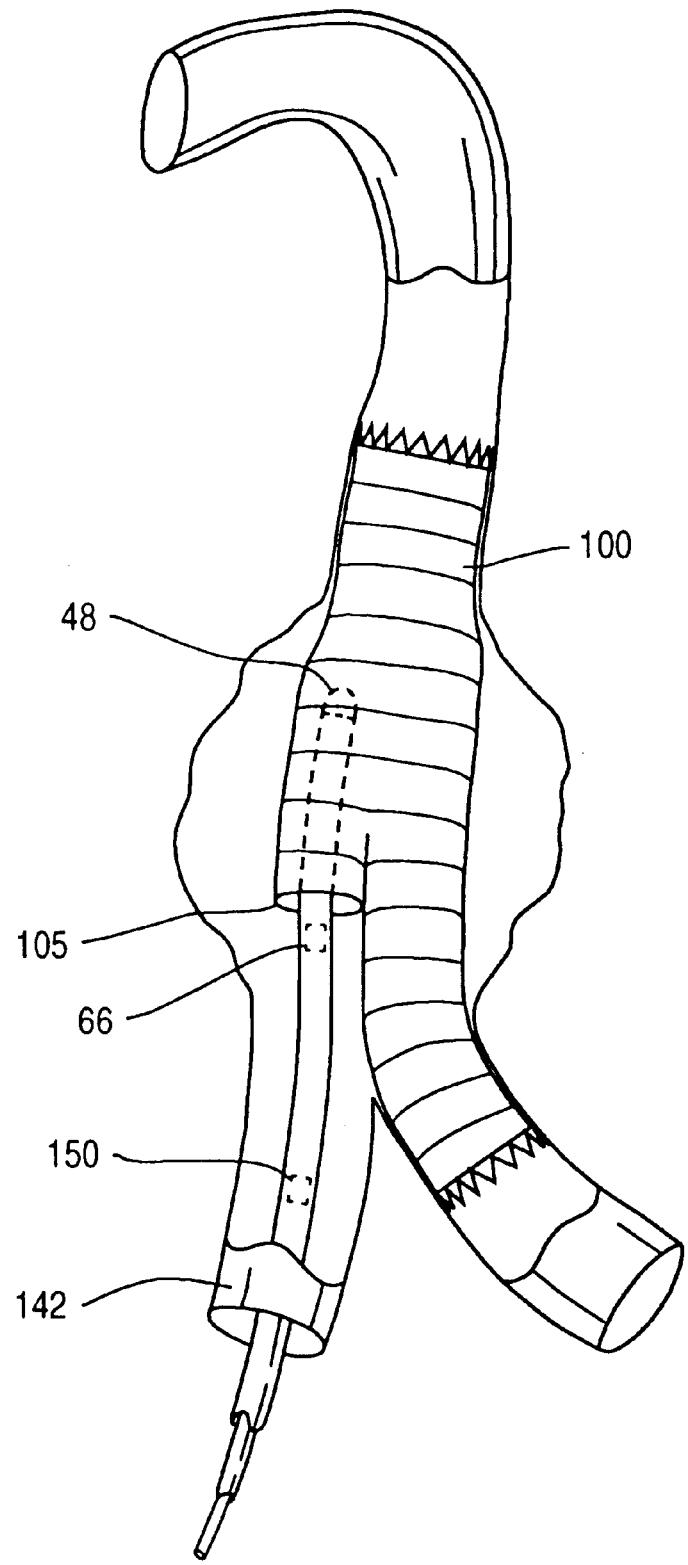

Referring now to FIG. 30, a secondary tubular prosthesis may be placed extending from branch 105 of branched prosthesis 100 down to second iliac 142. Delivery catheter 30 has a standard nosecone 48, as the rotational orientation is not critical. The distal and proximal ends of the prosthesis may be indicated by the nosecone 48 and proximal marker 150. It is preferable that marker ring 66 be located a predetermined distance proximal of the distal end of the prosthesis. Delivery catheter 30 is then axially positioned with marker ring 66 proximal of branch 105 to avoid the distal end of the prosthesis extending too far into branched graft 100 and folding over in the flow. Marker ring 66 thus acts as a safety marker.

Figure 31:
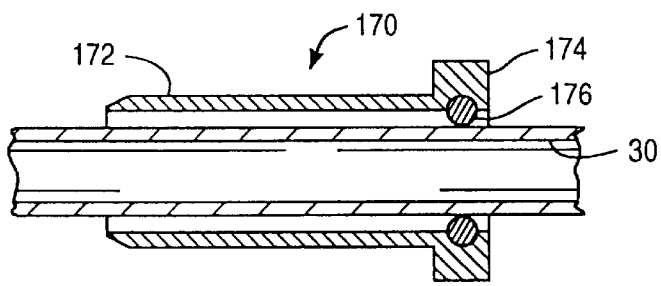
FIG. 31 is a cross-sectional view of a friction reducer tube disposed over the cover of the present delivery catheter.

The apparatus and methods of the present invention provide a cover which is smoothly retractable relative to a radially compressed prosthesis. However, a substantial amount of friction may be encountered at the introduction sheath where the present catheters enter a patient's body. Introduction sheaths must provide hemostasis for catheters and other invasive surgery apparatus of various sizes and configurations. Such introduction sheaths typically include a resilient sealing valve which radially compresses the outermost layer of the catheter. Such introduction sheath valves impose a substantial amount of friction against the catheter, making smooth withdrawal of a delivery catheter cover problematic. Therefore, the present invention further provides a friction reducer tube, as illustrated in FIG. 31.

Friction reducer tube 170 comprises a distally tapered tube 172, a proximal o-ring housing 174, and an o-ring 176. Tapered tube 172 is slightly larger in diameter than cover 30 of the present delivery catheter. 0-ring 176 provides hemostasis against the cover, but slides axially with little friction.

Figure 32:
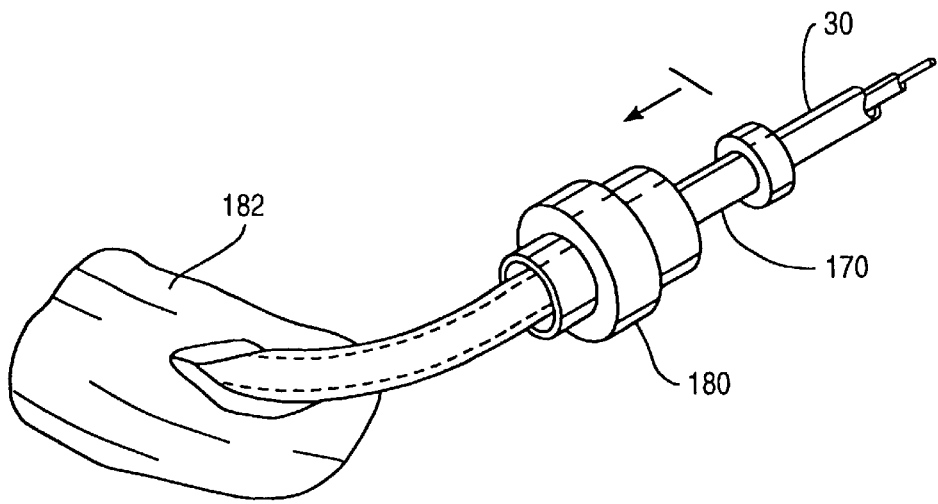
FIG. 32 illustrates the use of the friction reducer tube of FIG. 31 to reduce the friction of an introduction sheath valve during placement prostheses with the present delivery catheters.

Referring now to FIG. 32, an introduction sheath 180 is inserted into the patient body 182. Delivery catheter 30 is slidably disposed within friction reducer tube 170, and is introduced into the patient body through introduction sheath 180. Friction reducer tube 170 may then be slid distally so that the hemostasis valve rides over tapered tube 172. To deploy a tubular prosthesis, one surgeon retracts cover 30, while another surgeon manipulates the distal end of cover 32 relative to shaft 34, ideally using a mechanical advantage mechanism as illustrated in FIG. 10.

Figure 33:
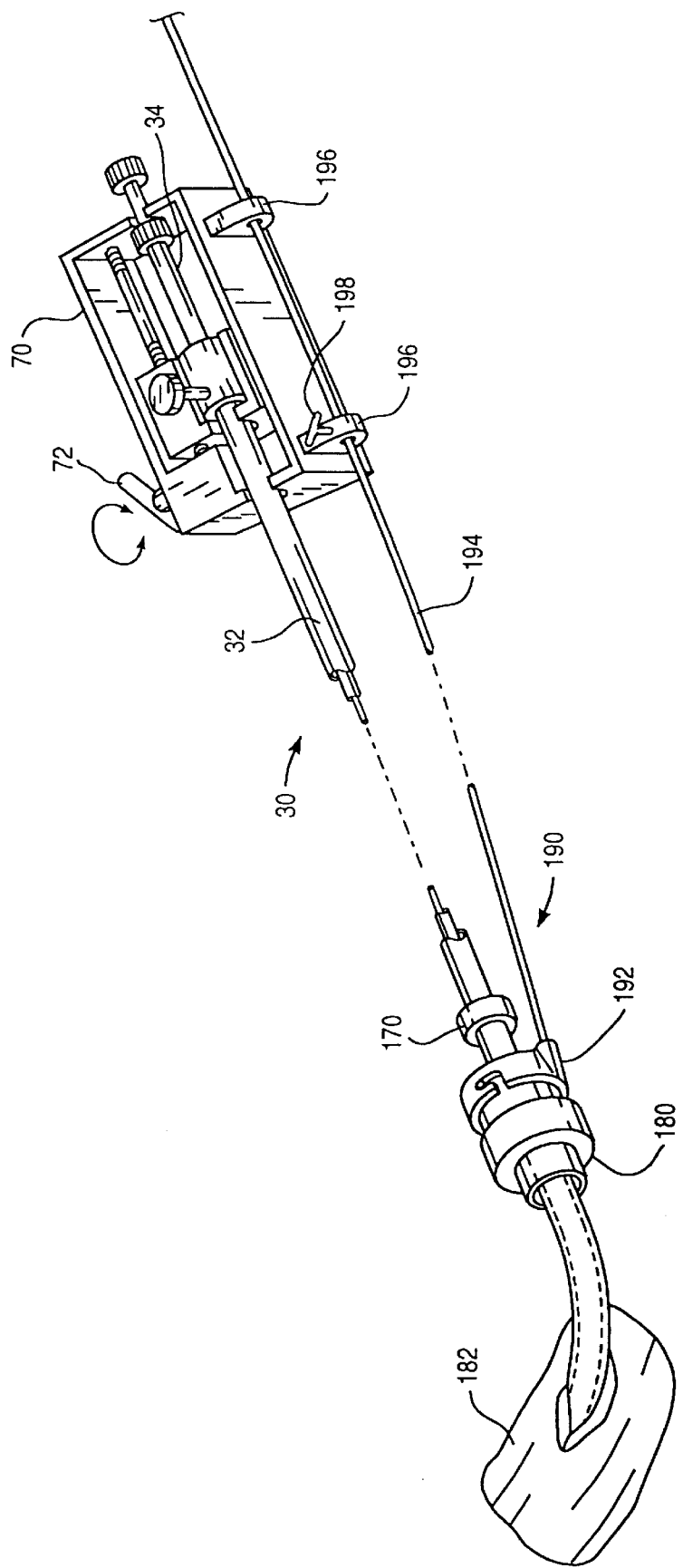
FIG. 33 illustrates a brace which prevents movement of housing 70 to restrain the prosthesis at a target location during deployment.

Referring now to FIG. 33, a brace 190 optionally restrains the prosthesis at the target location while withdrawing cover 32. Brace 190 attaches to introducer sheath 180 with a locking collar 192. Bar 194 extends proximally from locking collar 192, and is slidably received by tabs 196 protruding from housing 70. Once the prosthesis is positioned at the target location, a set screw 198 is tightened to fix the distance between the proximal end of delivery catheter 30 and the introduction sheath 180. Rotating handle 72 thus withdraws cover 30 proximally through introduction sheath 180 without distally advancing shaft 34. This minimizes the danger of advancing the exposed runners into the lumen wall during deployment, and thus allows deployment by a single surgeon. The compressive load on bar 194 is reduced by friction reducer tube 170.

A wide variety of compression bearing structures could be used in place of bar 190. A telescoping tube with single or multiple overlapping sections having set screws would eliminate the protruding proximal end of the rod. Such a telescoping tube may optionally surround catheter 30 between the introducer sheath and housing. Alternatively, a flexible tube having good column stiffness disposed over the delivery catheter also prevents axial movement of the prosthesis, and avoids the long, rigid, and potentially cumbersome bar structure. Such a flexible tube preferably comprises a tightly wound coil analogous to flexible shaft 35 shown in FIG. 9A. Although a fixed length tube may be used, telescoping flexible overlapped tubes, usually having a locking device such as set screws, compressive clamps, or the like, are preferred.

The brace of the present invention may advantageously be used with alternative proximal housings having a wide variety of mechanisms for translating the cover relative to the shaft, including electric motors, foot operated linkages, and the like.

Although the foregoing invention has been described in some detail by way of illustration and example, for purposes of clarity and understanding, certain changes and modifications will be obvious to those of skill in the art. For example, the present cover and/or runners may be attached to the elongate shaft as a cartridge, preferably preloaded with a prosthesis. Thus, the scope of the present invention is limited only by the appended claims.

What is claimed is:

1. An improved delivery catheter for placement of a branching, radially compressible prosthesis in a branching body lumen, the catheter of the type having an elongate shaft structure including a proximal end, a distal end, an axis therebetween, and a prosthesis receptacle near the distal end, the improvement comprising:

a rotation marker on the shaft structure adjacent to the prosthesis receptacle, the rotation marker having an asymmetric radiographic image, the image being asymmetric about the axis of the shaft structure.

2. An improved delivery catheter as claimed in claim 1, further comprising a branch axial marker on the shaft structure within the prosthesis receptacle.

3. An improved delivery catheter as claimed in claim 1, further comprising a proximal marker disposed a predetermined distance from the proximal end of the prosthesis receptacle and a distal marker disposed a predetermined distance from the distal end of the prosthesis receptacle, wherein the proximal and distal markers are radiopaque and are movable with the shaft.

4. An improved delivery catheter as claimed in claim 1, wherein the rotation marker includes a radiopaque body having a radiographically clear passage and a radiographically clear notch.

5. An improved prosthesis delivery catheter for placement of a secondary radially compressible prosthesis within a branch of a branching prosthesis, the branching prosthesis placed in a branching body lumen, the catheter of the type having an elongate shaft structure including a proximal end, a distal end, and a prosthesis receptacle near the distal end, the improvement comprising:

a radiopaque safety marker positioned on the distal end of the shaft structure a maximum insertion distance proximal of a distal end of the secondary prosthesis, wherein the maximum insertion distance corresponds to a maximum distance the secondary prosthesis can safely extend into the branch of the branching prosthesis.

6. An expandable tip delivery catheter for placement of a radially compressible prosthesis having a large diameter portion and a small diameter end, the catheter comprising:

an elongate flexible shaft having a proximal end, a distal end, and a prosthesis receptacle near the distal end; and a cover slidably disposed about the shaft, the cover comprising:

a body portion; and a resilient structure extending distally from the body portion, the resilient structure having an inherent cross-section which is smaller than the body portion;

wherein the resilient structure expands over the prosthesis receptacle as the cover is withdrawn proximally over the shaft.

7. An expandable tip delivery catheter as claimed in claim 6, wherein the resilient structure comprises a braided expandable mesh tubing and an elastomeric material disposed over the mesh tubing.

* * * * *